United States Patent [19]

Schneider

[11] 4,150,054
[45] Apr. 17, 1979

[54] N-AKYLATION OF AROMATIC AMINES IN THE PRESENCE OF AN ALIPHATIC AMINO COMPOUND

[75] Inventor: Joachim Schneider, Krefeld, Fed. Rep. of Germany

[73] Assignee: Bayer Aktiengesellschaft, Leverkusen, Fed. Rep. of Germany

[21] Appl. No.: 856,566

[22] Filed: Dec. 1, 1977

[30] Foreign Application Priority Data

Dec. 24, 1976 [DE] Fed. Rep. of Germany ....... 2658728

[51] Int. Cl.$^2$ ............................................ C07C 85/06
[52] U.S. Cl. ............................. 260/577; 260/567.6 M; 260/574; 260/583 R; 260/583 H; 260/584 R
[58] Field of Search ................................ 260/574, 577

[56] References Cited

U.S. PATENT DOCUMENTS

| 1,994,852 | 3/1935 | Carleton et al. ................. 260/577 X |
| 2,113,241 | 4/1938 | Punnett ............................ 260/577 X |
| 2,377,233 | 5/1945 | Hill et al. ............................. 260/577 |
| 2,419,718 | 4/1947 | Kehe ................................. 260/577 X |
| 3,957,874 | 5/1976 | Dockner et al. ...................... 260/577 |
| 3,969,411 | 7/1976 | Schneider ............................ 260/577 |
| 4,062,893 | 12/1977 | Kyuma et al. ....................... 260/577 |
| 4,067,903 | 1/1978 | Hoch et al. ....................... 260/577 X |

FOREIGN PATENT DOCUMENTS

| 553448 | 5/1943 | United Kingdom ..................... 260/577 |
| 812058 | 4/1959 | United Kingdom ..................... 260/577 |

OTHER PUBLICATIONS

Pinegina et al., "Chem. Ab.", vol. 78, Ab. No. 15401r (1973).

Primary Examiner—Winston A. Douglas
Assistant Examiner—John Doll
Attorney, Agent, or Firm—Sprung, Felfe, Horn, Lynch & Kramer

[57] ABSTRACT

An improvement in a process for the alkylation of an aromatic amine by contacting an aromatic amine with an alcohol in the presence of phosphoric acid, the improvement residing in including in the phosphoric acid an aliphatic amine containing at least one aliphatic radical having more then 3 carbon atoms, a phosphoric acid salt of said aliphatic amine or a quaternary ammonium salt of said aliphatic amine.

24 Claims, No Drawings

N-AKYLATION OF AROMATIC AMINES IN THE PRESENCE OF AN ALIPHATIC AMINO COMPOUND

The invention relates to a particularly advantageous process for N-alkylating aromatic amines by reacting the amines with alcohols in the presence of phosphoric acid.

It is known to alkylate aniline in a manner in which a mixture of alcohol and aniline is passed through hot concentrated phosphoric acid (German Pat. No. 1,031,796). A disadvantage of the process is that, industrially, N,N-dialkyl compounds, especially those containing alkyl radicals other than methyl, can be prepared only poorly. A further disadvantage is that after some time the phosphoric acid loses its catalytic activity.

It has now been found that N-alkylated aromatic amines can be obtained in a particularly simple and economical manner by heating the aromatic amines with lower aliphatic alcohols in the presence of phosphoric acid, the aromatic amine and an alcohol being passed through heated phosphoric acid, the alkylation being carried out in the presence of an aliphatic amine containing at least one aliphatic radical with more than 3 carbon atoms.

Aliphatic amines of the general formula

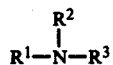
(I)

in which
$R^1$ denotes a straight-chain or branched, saturated or unsaturated aliphatic radical with 4 to 20 carbon atoms and
$R^2$ and $R^3$ are identical or different and represent hydrogen or a straight-chain or branched, saturated or unsaturated aliphatic radical with up to 20 carbon atoms, are preferably used. Preferably $R^1$, $R^2$ and $R^3$ are independently alkyl or alkenyl groups.

Examples of these which may be mentioned are: butylamine, isobutylamine, hexylamine, octylamine, 2-ethylhexylamine, decylamine, dodecylamine, tetradecylamine, hexadecylamine, octadecylamine, eicosylamine or oleylamine; dibutylamine, di-isobutylamine, dihexylamine, dioctylamine, di-(2-ethylhexyl)-amine, didodecylamine or distearylamine; or tri-n-butylamine, dimethyl-laurylamine or dimethyl-stearylamine.

Instead of the abovementioned aliphatic amines, the phosphoric acid salts of these amines can, of course, also be used. Furthermore, instead of the amines mentioned, their quaternary ammonium salts, which can be obtained, for example, by reaction with alkyl chlorides, alkyl sulphates, alkylbenzenesulphonates, alkyl phosphates, alkyl phosphites or aralkyl chlorides, can be used.

Examples of compounds which may be mentioned with which the quaternisation to give the abovementioned quaternary salts can be carried out are: methyl chloride, ethyl chloride, propyl chloride, butyl chloride, benzyl chloride, pentyl chloride, hexyl chloride, octyl chloride, decyl chloride, dodecyl chloride, dimethyl sulphate, diethyl sulphate, dipropyl sulphate, benzenesulphonic acid methyl ester, benzenesulphonic acid ethyl ester, benzenesulphonic acid propyl ester, o, p-toluenesulphonic acid methyl ester, o, p-toluenesulphonic acid ethyl ester, o,p-toluenesulphonic acid propyl ester, trimethyl phosphate, triethyl phosphate, tripropyl phosphate, dimethyl phosphite or diethyl phosphite.

These alkylammonium salts preferably correspond to the general formula

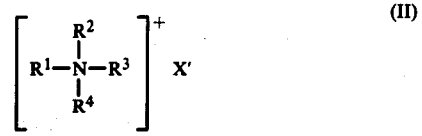

in which
$R^1$, $R^2$ and $R^3$ have the meaning indicated above,
$R^4$ represents hydrogen, alkyl or aralkyl and
$X'$ denotes an anion.
$R^4$ preferably represents alkyl with 1 to 12, preferably 1 to 8 and in particular 1 to 4, carbon atoms and aralkyl with 6 or 10 carbon atoms in the aromatic part and 1 to 4 carbon atoms in the aliphatic part.

Possible examples of the anion (X) are: halide, preferably chloride, bisulphate, sulphate, dihydrogen phosphate, hydrogen phosphate, phosphate, dihydrogen phosphite and hydrogen phosphite, as well as anions of the formulae $R^5SO_4'$, $R^5_2PO_4'$, $R^5HPO_4'$, $R^5PO_4''$ and $R^5HPO_3'$, in which $R^5$ represents alkyl or aralkyl in the same scope of meaning as for $R^4$, and furthermore benzenesulphonate and o- and p-alkylbenzene-sulphonate, the alkyl group having up to 12, preferably up to 4, carbon atoms; methyl and ethyl may be mentioned in particular.

Aromatic amines from the aniline series, including the corresponding derivatives substituted in the nucleus, as long as they are sufficiently volatile at the reaction temperatures, can be used for carrying out the process according to the invention. In general, with respect to the substitution there is only the limitation that the substituents may not be and/or contain those groups and/or radicals which themselves react under the conditions of the process according to the invention.

Examples which may be mentioned of substituents by which the aromatic amines can be substituted are: halogen (fluorine, bromine, chlorine and iodine), preferably fluorine, chlorine and bromine, and lower alkyl, alkoxy and alkylmercapto radicals with 1 to 4, preferably 1 or 2, carbon atoms.

The aromatic amines can, of course, also be poly-substituted by the abovementioned substituents, in particular halogen, alkyl and alkoxy, disubstitution by identical or different substituents being possible in particular.

The most important aromatic amines which can be used correspond to the general formula

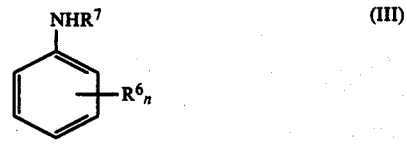

in which
$R^6$ represents halogen or a lower alkyl, lower alkoxy or lower alkylmercapto radical.
$R^7$ represents hydrogen or a lower alkyl radical and n denotes one of the numbers 0, 1, 2 or 3, it also being possible for the radicals $R^6$ to be different in the case where n represents 2 or 3.

Those aromatic amines in which $R^6$ represents chlorine, methyl or ethyl, $R^7$ represents hydrogen, methyl or ethyl and n is 0, 1 or 2, in particular 0 or 1, are preferably used as the starting material.

Representative examples which may be mentioned of the aromatic amines which can be alkylated by the process according to the invention are: aniline, o-, m- and p-toluidine, the xylidines and chlorine-substituted anilines.

Possible alcohols, which are used in the process according to the invention, are, preferably, lower aliphatic alcohols with 1 to 5 carbon atoms, in particular methanol and ethanol.

In general, the reaction is carried out with an excess of alcohol above the amount required stoichiometrically. The excess can be up to 2,000, preferably up to 500 and in particular up to 250, mol % of the amount required stoichiometrically.

The excess, unreacted alcohol can, of course, be used again, if appropriate after removing the water, formed during the reaction, contained therein.

The reaction temperature of the process according to the invention is between 150 and 300° C, preferably 170 to 280° C and in particular between 180 and 250° C.

The amount of phosphoric acid which is employed in the process according to the invention is not critical. It is chosen according to the size of the apparatus and the throughput rate of the mixture of amine to be alkylated and alcohol; the optimum amount can be easily determined by preliminary experiments.

Generally speaking the phosphoric acid is present in an amount between 30 and 85 weight percent of the reaction mixture, preferably between 40 and 75 weight percent.

Likewise, the concentration of the phosphoric acid which is used in the process according to the invention is not critical, since any water which may be contained in its distils off at the reaction temperature and is continuously reformed as a by-product of the reaction, which may be indicated summarisingly here by the example of aniline and methanol,

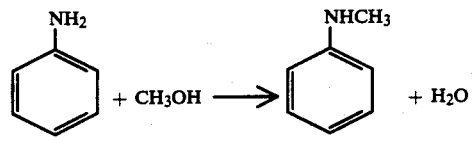

and is distilled off.

Aqueous phosphoric acid with a content of between 50 and 100% by weight of $H_3PO_4$ can be used. Easily accessible concentrated phosphoric acid is preferably used, such as is commercially available, containing 70 to 90, preferably 85 to 89, % by weight of $H_3PO_4$. Methaphosphoric acid and polyphosphoric acids can, of course, also be used; their use depends on whether they are sufficiently mobile at the reaction temperature.

An essential characteristic of the process according to the invention is the presence of an aliphatic amine containing at least one aliphatic radical with more than 3 carbon atoms, it also being possible, as stated above, for a phosphoric acid salt or a quaternary ammonium salt of this amine to be used instead of this amine. Mixtures of appropriate amines and/or ammonium salts can, of course, also be used.

The above-mentioned amines and/or ammonium salts can be added to the phosphoric acid before or after the start of the reaction. The addition can be made all at once or by metering in over a longer period of time. It is also possible to add the above-mentioned amines and/or ammonium salts to the phosphoric acid only after it has been used for a relatively long period.

The amine and/or ammonium salt is used in an amount between 0.1 and 150% by weight, preferably between 2 and 100% by weight and in particular between 3 and 75% by weight, relative to the phosphoric acid.

The amount of amine and/or ammonium salt which is appropriately added can depend both on its nature and on the aromatic amine to be alkylated and the alcohol used. The optimum amount can be easily determined by a few preliminary experiments.

The carrying out of the process according to the invention is simple and can be effected in accordance with the process of German Pat. No. 1,031,796.

For example, the phosphoric acid, together with the appropriate amount of the aliphatic amine and/or ammonium salt according to the invention, can be filled into an upright tube, which widens at the upper end for the separation of the gaseous and liquid phase. The sequence in which the phosphoric acid and the amine and/or ammonium salt are introduced is not critical. The aromatic amine to be alkylated and the alcohol are then fed in, in the liquid or gaseous state, at the lower end of the reaction tube at the appropriate reaction temperature and the gaseous reaction products issuing from the mixture of phosphoric acid and aliphatic amine and/or ammonium salt are removed at the upper end and worked up in the customary manner, for example, by fractional condensation or by complete condensation and subsequent fractional distillation, if appropriate under reduced pressure.

In general, the reaction proceeds exothermically so that the reaction apparatus is heated or cooled, depending on the size, rate of reaction, heat transfer and other decisive factors. It can be advantageous to introduce the aromatic amine to be reacted in the liquid state, if appropriate after melting. The alcohol can be introduced in the liquid or gaseous state. The aromatic amine and alcohol can, of course, be introduced into the reaction apparatus already as a mixture, but also separately. It is also possible to already heat up the two reactants, before introducing them into the reaction apparatus, to such an extent that supply or removal of heat is not necessary to maintain the desired reaction temperature. The appropriate construction of the apparatus is the state of the art.

In carrying out the process for dialkylation, in particular, it can be advantageous not to aim for a complete reaction, so that the reaction product still contains monoalkylated aromatic amine and, if appropriate, also unreacted aromatic amine, in addition to the dialkylated aromatic amine. The separation of the reaction products can then be carried out in a known manner according to the state of the art and monoalkylated aromatic amine and, if appropriate, unreacted aromatic amine can be recycled into the reaction apparatus, as can the unreacted excess alcohol. By appropriately choosing the conditions, a constant ratio between mono- and di- alkylated aromatic amine to accord with an existing requirement can also be established, which can then be particularly advantageous.

The process according to the invention is particularly suitable for the N-methylation and N-ethylation of aromatic amines and can preferably be used for the preparation of corresponding N,N-dialkylamines. As is known, these are valuable intermediate products for the preparation of plant protection agents and dyestuffs.

Compared with the state of the art, the process according to the invention has the advantage that a higher degree of conversion, and in particular higher proportion of N,N-dialkylamines, is obtained. The space/time yield is increased and thus there is the possibility of making better use of a given reaction volume or, stated otherwise, of reacting larger amounts in a smaller reaction volume.

In the process according to the state of the art, in which aromatic amine and alcohol are passed through heated phosphoric acid, the degree of conversion, that is to say the ratio of alkylated aromatic amine to aromatic amine employed, depends on various reaction parameters, for example on the reaction temperature, on the molar ratio in which the aromatic amine and alcohol are employed, the level of the phosphoric acid layer, the residence time of the starting materials employed and the reaction products in the phosphoric acid, the state of division of the starting materials on entering and passing through the heated phosphoric acid and, finally, on the catalytic activity of the heated phosphoric acid.

Whether a monoalkylation or dialkylation of the aromatic amine employed is achieved also depends on these factors.

In principle, it is thus possible, as the Examples of German Pat. No. 1,031,796 show, to obtain dimethylaniline, for example, in a yield of over 90%.

In carrying out the examples which follow, achieving complete reaction and complete dialkylation has been dispensed with. In fact, under otherwise identical conditions, the catalytic activity from adding, according to the invention, an aliphatic amine to the phosphoric acid and thus the technical advance of the process according to the invention can already be shown by the increase in the conversion or dialkylation, under otherwise identical conditions.

EXAMPLES

In the examples which follow the same reaction apparatus was used in each case. It consisted of a 2 l three-necked flask provided with a tube, placed on the bottom, of 4 cm in diameter and 1 m in length which served as the reaction tube and was heated externally. A tube of 6 mm in diameter, through which the mixture of the starting compounds was fed, was passed through one neck of the three-necked flask to the bottom of the reaction tube. The second neck of the three-necked flask was provided with a bridge which was connected, via a descending cooler, to a receiver for collecting the reaction products. A thermometer for monitoring the reaction temperature was introduced through the third neck of the three-necked flask and its mercury bulb was approximately halfway up the reaction tube.

This apparatus was charged with phosphoric acid and the aliphatic amine and/or its ammonium salt, as indicated in each case in the examples which follow.

After heating to the chosen reaction temperature, the mixture of the aromatic amine to be alkylated and the alcohol, indicated in each case in the examples which follow, was passed in at the rate indicated.

After 10 hours in each case, the reaction product which was obtained in these 10 hours and collected in the receiver was removed and analysed by gas chromatography, the excess alcohol and water formed not having been taken into account in the evaluation.

In the examples which follow, the composition of the reaction product which was constant for a relatively long time after the end of the starting-up period is indicated.

EXAMPLE 1

The apparatus was charged with 1,200 g of 85% strength by weight aqueous phosphoric acid and the amount indicated in Table I which follows of the amine or ammonium salt, also indicated.

400 ml of a mixture of 40% by weight of aniline and 60% by weight of ethanol per hour were then passed through at 220° C.

In Table I which follows, the composition of the reaction product under stationary conditions, as given above, is also indicated in each case.

Table I

| Example No. | Phosphoric acid (85% by weight of $H_3PO_4$) g | Amine or ammonium salt g | | Reaction product | | |
|---|---|---|---|---|---|---|
| | | | | N-ethylaniline % | N,N-diethylaniline % | aniline % |
| 1.1 | 1,000 | 300 | di-n-butylamine | 50 | 22 | 28 |
| 1.2 | 1,000 | 300 | di-iso-butylamine | 51 | 19 | 30 |
| 1.3 | 1,000 | 300 | tri-n-butylamine | 50 | 23 | 27 |
| 1.4 | 1,000 | 300 | n-octylamine | 48 | 28 | 24 |
| 1.5 | 1,000 | 300 | 2-ethyl-hexylamine | 47 | 27 | 26 |
| 1.6 | 1,000 | 300 | di-2-ethyl-hexylamine | 48 | 30 | 22 |
| 1.7 | 1,000 | 300 | di-n-hexylamine | 49 | 28 | 23 |
| 1.8 | 1,000 | 300 | n-dodecylamine | 44 | 36 | 20 |
| 1.9 | 1,000 | 50 | stearylamine | 49 | 20 | 31 |
| 1.10 | 1,000 | 90 | oleylamine | 49 | 22 | 29 |
| 1.11 | 1,000 | 50 | 2-ethyl-n-hexylamine | 50 | 22 | 28 |
| 1.12 | 1,000 | 100 | 2-ethyl-n-hexylamine | 49 | 24 | 27 |
| 1.13 | 1,000 | 200 | 2-ethyl-n-hexylamine | 48 | 27 | 25 |
| 1.14 | 1,000 | 450 | 2-ethyl-n-hexylamine | 47 | 29 | 24 |
| 1.15 | 1,000 | 100 | mixture + | 48 | 30 | 22 |
| 1.16 | 1,000 | 200 | di-(β-hydroxyethyl)-oleylamine | 49 | 19 | 32 |
| 1.17 | 1,000 | 200 | reaction product + | 49 | 25 | 26 |
| 1.18 (Comparison) | 1,000 | — | — | 15 | 15 | 34 |

For Table I

+The mixture used in Example 1.15 consisted of 7% of $C_8$-n-alkylamine, 6% of $C_{10}$-n-alkylamine, 51% of $C_{12}$-n-alkylamine, 19% of $C_{14}$-n-alkylamine, 8% of $C_{16}$-n-alkylamine and 9% of $C_{18}$-n-alkylamine. The reaction product used in Example 1.17 was obtained by reaction of dimethyl-laurylamine and trimethyl phosphate.

EXAMPLE 2

The reaction apparatus was charged with the amount, indicated in Table II, of 85% strength by weight aqueous phosphoric acid and the indicated amount of amine. 400 ml of a mixture of 40% by weight of aniline and 60% by weight of methanol per hour were then passed through at 220° C.

The composition of the reaction product under stationary conditions is also given in the Table.

Table II

| Example No. | Phosphoric acid 85% by weight of $H_3PO_4$ g | g | Amine | Reaction product | | |
|---|---|---|---|---|---|---|
| | | | | N-methylaniline % | N,N-dimethylaniline % | aniline % |
| 2.1 | 1,100 | 100 | 2-ethyl-hexylamine | 8 | 88 | 4 |
| 2.2 | 1,000 | 200 | di-(2-ethyl-hexylamine | 9 | 87 | 4 |
| 2.3 (Comparison) | 1,200 | — | — | 13 | 80 | 7 |

EXAMPLE 3

The reaction apparatus was charged with 1,000 g of 85% strength by weight aqueous phosphoric acid and 200 g of 2-ethyl-hexylamine. 600 ml of a mixture of 40% by weight of toluidine and 60% by weight of methanol per hour were fed in at 220° C.

For comparison, the experiment was repeated, the reaction apparatus having been charged, only with 1,200 g of 85% strength by weight phosphoric acid.

These two experiments were each carried out with o-, m- and p-toluidine.

In Table III which follows, the composition of the reaction product under stationary conditions is given for the experiment and the comparison experiment in each case.

Table III

| Example No. | Starting compound | Reaction product | | |
|---|---|---|---|---|
| | | N-methyl compound % | N,N-dimethyl compound % | non-methylated starting compound % |
| 3.1 | o-toluidine | 18 | 71 | 11 |
| 3.2 (comparison) | " | 23 | 65 | 12 |
| 3.3 | m-toluidine | 8 | 87 | 5 |
| 3.4 (comparison) | " | 11 | 82 | 7 |
| 3.5 | p-toluidine | 9 | 85 | 6 |
| 3.6 (comparison) | " | 12 | 80 | 8 |

EXAMPLE 4

(4.1) The reaction apparatus was charged with a mixture of 1,000 g of 85% strength by weight aqueous phosphoric acid and 200 g of dodecylamine.

500 ml of a mixture of 30% by weight of aniline and 70% by weight of n-butanol per hour were then passed through at 220° C.

Under stationary conditions, the reaction product consisted of 45% of N,N-di-n-butylamine, 40% of N-n-butylamine and 15% of aniline.

(4.2) (Comparison)

The experiment according to 4.1 was repeated, but with the difference that only 1,200 g of 85% strength by weight phosphoric acid were initially filled into the reaction apparatus.

The analysis of the reaction product gave 20% of N,N-di-n-butylamine, 52% of N-n-butylaniline and 28% of aniline.

EXAMPLE 5

Example 1.14 was repeated, with the only difference that the reaction temperature was 260 instead of 220° C.

The reaction product had the following composition: 34% of N,N-diethylaniline, 50% of N-ethylaniline and 16% of aniline.

EXAMPLE 6

Example 1.18 was repeated, with the only difference that the reaction temperature was 200 instead of 220° C.

The reaction product had the following composition: 22% of N,N-diethylaniline, 41% of N-ethylaniline and 37% of aniline.

What we claim is:

1. In a process for the N-alkylation of an aromatic amine by contacting said aromatic amine with an alcohol in the presence of phosphoric acid, the aromatic amine and alcohol being passed through heated phosphoric acid, the improvement which comprises including in said heated phosphoric acid an aliphatic amine containing at least 1 aliphatic radical with more than 3 carbon atoms, a phosphoric acid salt of said aliphatic amine or a quaternary ammonium salt of said aliphatic amine.

2. A process according to claim 1 wherein an aliphatic amine is included in said phosphoric acid and said aliphatic amine has the formula

(I)

wherein
R$^1$ denotes a straight-chain or branched saturated or unsaturated aliphatic radical having 4 to 20 carbon atoms and
R$^2$ and R$^3$ are identical or different and represent a hydrogen atom or a straight or branched saturated or unsaturated aliphatic radical with up to 20 carbon atoms.

3. A process according to claim 1 wherein a phosphoric acid salt of an aliphatic amine of the formula

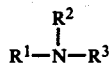 (I)

wherein
R¹ denotes a straight-chain or branched saturated or unsaturated aliphatic radical having 4 to 20 carbon atoms and
R² and R³ are identical or different and represent a hydrogen atom or a straight or branched saturated or unsaturated aliphatic radical with up to 20 carbon atoms, is used.

4. A process according to claim 1 wherein a quaternary ammonium salt of an aliphatic amine is employed said quaternary ammonium salt having the formula

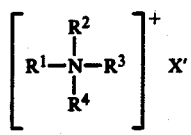

wherein R¹, R² and R³ have the meanings given in claim 1 and R⁴ denotes a hydrogen atom or an alkyl or aralkyl group and X' denotes an anion.

5. A process according to claim 4 wherein R⁴ denotes a $C_1$ to $C_4$ alkyl group or an aralkyl group having 6 to 10 carbon atoms in the aromatic part and 1 to 4 carbon atoms in the aliphatic part.

6. A process according to claim 1 wherein the aliphatic amine, phosphoric acid salt or quaternary ammonium salt is employed in an amount between 0.1 and 150% by weight, based upon the weight of said phosphoric acid.

7. A process according to claim 6 wherein the aliphatic amine, phosphoric acid salt of amine or quaternary ammonium salt of amine is employed in an amount between 3 and 75% be weight based upon the weight of said phosphoric acid.

8. A process according to claim 1 wherein the reaction is carried out at a temperature in the range of between 150 and 300° C.

9. A process according to claim 1 wherein said aromatic amine has the formula

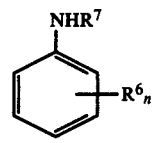 (III)

wherein $R^6$ denotes a halogen atom or a lower alkyl, lower alkoxy or lower alkylmercapto radical, $R^7$ denotes a hydrogen atom or a lower alkyl radical and n is 0, 1, 2 or 3, the radical $R^6$ being the same or different when n is 2 or 3.

10. A process according to claim 9 wherein $R^6$ denotes a chlorine atom or a methyl or ethyl group, $R^7$ denotes a hydrogen atom or a methyl or ethyl group and n is 0, 1 or 2.

11. A process according to claim 9 wherein the aromatic amine is aniline, o-toluidine, m-toluidine, p-toluidine, a xylidine or a chlorine substituted aniline.

12. A process according to claim 1 wherein to the phosphoric acid there is added di-n-butylamine.

13. A process according to claim 1 wherein to the phosphoric acid there is added di-iso-butylamine.

14. A process according to claim 1 wherein to the phosphoric acid there is added tri-n-butylamine.

15. A process according to claim 1 wherein to the phosphoric acid there is added n-octylamine.

16. A process according to claim 1 wherein to the phosphoric acid there is added 2-ethyl-hexylamine.

17. A process according to claim 1 wherein to the phosphoric acid there is added di-2-ethyl-hexylamine.

18. A process according to claim 1 wherein to the phosphoric acid there is added di-n-hexylamine.

19. A process according to claim 1 wherein to the phosphoric acid there is added N-dodecylamine.

20. A process according to claim 1 wherein to the phosphoric acid there is added stearylamine.

21. A process according to claim 1 wherein to the phosphoric acid there is added oleylamine.

22. A process according to claim 1 wherein to the phosphoric acid there is added 2-ethyl-n-hexylamine.

23. A process according to claim 1 wherein to the phosphoric acid there is introduced a mixture of $C_{8\text{-}n\text{-}alkylamine}$, $C_{10\text{-}n\text{-}alkylamine}$, $C_{12\text{-}n\text{-}alkylamine}$, $C_{14\text{-}n\text{-}alkylamine}$, $C_{16\text{-}n\text{-}alkylamine}$ and $C_{18\text{-}n\text{-}alkylamine}$.

24. A process according to claim 1 wherein to the phosphoric acid there is added di-($\beta$-hydroxyethyl)-oleylamine.

* * * * *